United States Patent [19]

Giesa et al.

[11] Patent Number: 5,514,376

[45] Date of Patent: * May 7, 1996

[54] CELL CULTURE OF HEPATITS A VIRUS

[75] Inventors: Paula A, Giesa; Philip J. Provost, both of Lansdale; Maurice R. Hilleman, Lafayette Hill, all of Pa.

[73] Assignee: Merck & Co., Inc., Rayway, N.J.

[ * ] Notice: The portion of the term of this patent subsequent to Jun. 4, 2008, has been disclaimed.

[21] Appl. No.: 16,486

[22] Filed: Feb. 10, 1993

Related U.S. Application Data

[63] Continuation of Ser. No. 712,365, Jun. 10, 1991, which is a continuation of Ser. No. 126,458, Nov. 27, 1987, abandoned, which is a continuation-in-part of Ser. No. 609,677, May 14, 1984, Pat. No. 5,021,348, which is a continuation of Ser. No. 437,095, Oct. 27, 1982, abandoned, which is a continuation-in-part of Ser. No. 71,648, Sep. 4, 1979, abandoned.

[51] Int. Cl.$^6$ .............................. A61K 39/12; C12N 7/00; C12N 7/08

[52] U.S. Cl. .................................. 424/204.1; 435/235.1; 435/237

[58] Field of Search .................................. 424/89, 204.1; 435/235.1, 237

[56] References Cited

U.S. PATENT DOCUMENTS

| | | |
|---|---|---|
| 3,105,011 | 9/1963 | McLean et al. |
| 3,354,038 | 11/1967 | Bass et al. |
| 3,432,391 | 3/1969 | Hays et al. |
| 3,470,294 | 9/1969 | Drager et al. |
| 3,520,972 | 7/1970 | Smith et al. |
| 3,871,954 | 3/1975 | Zuckerman |
| 3,935,066 | 1/1976 | Apostolov |
| 4,029,764 | 6/1977 | Provost et al. |
| 4,031,203 | 6/1977 | Provost et al. |
| 4,053,582 | 10/1977 | Stickl |
| 4,058,598 | 11/1977 | Stern et al. |
| 4,164,566 | 8/1979 | Provost et al. |
| 4,506,016 | 3/1985 | Flehmig |
| 4,532,215 | 7/1985 | Daemer et al. |
| 4,614,793 | 9/1986 | Hughes et al. |
| 4,783,407 | 11/1988 | Provost et al. |
| 4,844,228 | 1/1990 | Purcell et al. |
| 5,021,348 | 6/1991 | Giesa et al. |

FOREIGN PATENT DOCUMENTS

| | | |
|---|---|---|
| 2398504 | 2/1979 | European Pat. Off. |
| 0025745 | 3/1981 | European Pat. Off. |
| 0074119 | 6/1987 | European Pat. Off. |
| 811411 | 4/1959 | United Kingdom |
| 878704 | 10/1961 | United Kingdom |

OTHER PUBLICATIONS

Siegl, "Replication of Hepatitis A Virus and Processing of Proteins," Vaccine 10 Suppl 1, S32–S34 (1992).

Emerson et al., "Molecular Basis of Virulence and Growth . . . ," Vaccine 10, Suppl 1, S36–S39 (1992).

Lemon et al., "Genetic, Antigenic and Biological Differences Between Strains . . . ," Vaccine 10, Suppl 1, S40–S44 (1992).

Houdt, "Possible Approaches to Develop Vaccines Against Hepatitis A, " Vaccine 10, Suppl 1, S48–S52 (1992).

Tedeschi et al., "Partial Characterization of Hepatitis A . . . , " J. Med Virol. 39:16–22 (1993).

Peetermans, "Production, Quality Control and Characterization . . . , " Vaccine 10, suppl 1, S99–S101 (1992).

Just et al., "Reactogenicity and Immunogenicity of Inactivated . . . , " Vaccine 10, Suppl 1, S110–S113.

Sjogren, "Clinical and Laboratory Observations . . . , " Vaccine 10, Suppl 1, S135–S137 (1992).

"Hepatitis A Vaccine: Development, Safety & Immunogenicity," Vaccine 10, Suppl 1, S146–S147 (1992).

Frösner et al., "Propagation of Human Hepatitis A Virus in a Hepatoma Cell Line," Infection 7:303—305 (1979).

Siegl et al., "Propagation and Assay of Hepatitis A Virus in Vitro," J. Virol Meth. 9:53–67 (1984).

Melnick et al., "Properties and Classification of Hepatitis A Virus," Vaccine 10: Suppl 1 S24–S26 (1992).

Balayan, "Natural Hosts of Hepatitis A Virus, " Vaccine 10: Suppl 1, S27–31 (1992).

Provost et al., "An Inactivated Hepatitis A Viral Vaccine . . . ," J. Med. Virol. 19:23–31 (1986).

Jansen et al., "Complete Nucleotide Sequence of A Cell Culture . . . , " Virology 163:299–307 (1988).

Cohen et al., "Complete Nucleotide Sequence of Wild–Type Hepatitis A Virus . . . , " J. Virol 61:50–59 (1987).

Cohen et al., "Complete Nucleotide Sequence . . . " Proc. Natl. Acad Sci 84:2497–2501 (1987).

Ross et al., "Nucleotide Sequence of High–Passage . . . , " J. Gen. Virol 70: 2805–2810 (1989).

Rightsel et al. Science, 124, pp. 226–228 (1956).

O'Malley et al. Proc. Soc. Exp. Biol. Med., 108, pp. 200–205 (1961).

Liebhaber et al. J. Exp. Med., 122, p. 1135, (1965).

O'Malley, et al., Proc. Nat. Acad. Sci., 56, p. 895 (1965).

Mirkovic et al., Proc. Soc. Exp. Biol. Med., 138, p. 626, (1971).

Advances in Viral Hepatitis, W.H.O. Tech. report, Series No. 602, (1977).

Dienstag et al., Intervirl., 6, p. 319, (1976).

Provost et al., Pro. Soc. Exp. Bio. & Med., 160, p. 213 (1979).

Provost et al., Biol. Abstract, 68, ref. No. 12885.

Feinstone et al., J. of Vir., 13, No. 6, pp. 1412–1414 (1974).

Feinstone et al., Science, 182, pp. 1026–1028 (1973).

Frosner et al., Infection, 7, 303–305 (1979).

Zuckerman, Nature, 279, p. 579 (1979).

Purcell et al. Am. J. Med. Sci. 270, 61–71 (1975).

McCollum, J. of Med. Virology 8: 1–29 (1981).

(List continued on next page.)

Primary Examiner—Michael P. Woodward
Attorney, Agent, or Firm—Joanee M. Giesser; Jack L. Tribble

[57] ABSTRACT

Hepatitis A virus is attenuated in virulence by in vitro passage in susceptible cell cultures, without prior passage in a subhuman primate. This process results in a live, attenuated hepatitis A virus vaccine suitable for human disease prevention.

2 Claims, No Drawings

OTHER PUBLICATIONS

Flehming et al. Med. Micro. Immunol. 170: 83–89 (1981).
Ed. Gerety, R. J. Hepatitis A pp. 247–261 Acad. Press (1984).
Ed. Gerety, R. J. Hepatitis A pp. 33–46 Acad. Press (1984).
Bradley, et al., Char. of Hepatitis A Virus, pp. 876–889, (1976).
Deinhardt, et al. Int. Symp. O. Viral Hep. Milon, Dev. Biol. Stand., 30, 390–404 (1975).
Almond Attn. of Poliovirus Neurovirulence, 41: 153–180 (1987).
Westrop et al. J. Of Virl. 63: 1338–1344 (1989).
Gauss–Muller et al. J. of Med. Vir. 7: 233–239 (1981).
Cann et al. Nucleic Acids Research 12: 7787–7792 (1984).
Pilipenko et al. Virology 168: 201–209 (1989).
Monica et al. J. of Virology pp. 515–525 (1986).
Kawamura et al. J. of Virology pp. 1302–1309 (1989).
Siegl et al. J. of Virology pp. 40–47 (1978).
Frosner et al. J. of Med. Vir. 1: 163–173 (1977).
Lennette, et al. eds; Diag. Proc. For Viral Rickettsial and Chlamydial Inf. 5th ed, p. 907 (1979).
Kojima et al, J. Med. Virol, 7, 273–286 (1981).
Provost et al. J. Med. Virol, 20, 165–175 (1986).
Robertson et al, J.I.D., 163, 286–292 (1991).
Provost, et al., P.S.E.B.M. 142, 1257 (1974).
Mascoli et al., P.S.E.B.M. 142, 276 (1973).
Dienstag, et al. Lancet, 705, Apr. 5, 1975.
Flehmig et al., Viral Hepatitis and Liver Disease, 87–90 (1988).
Flemig et al, Viral Hepatitis and Liver Disease, 100–105 (1988).
Flehmig et al., 3, Med. Viral 22, 7–16 (1987).
Provost, P. J. and Hilleman, M. R. Hepatitis Scientific Memoranda, Memo H–1531, early Feb. 1979.

CELL CULTURE OF HEPATITS A VIRUS

RELATED APPLICATIONS

This is a continuation of application Ser. No. 07/712,365 filed on Jun. 6, 1991, which patent application is a continuation of patent application U.S. Ser. No. 126,458, filed 27 Nov. 1987, now abandoned; which was a continuation-in-part of patent application U.S. Ser. No. 609,677 filed 14 May 1984, now U.S. Pat. No. 5,021,348, issued 04 Jun. 1991 ; which was a continuation of patent application U.S. Ser. No. 437,095 filed 27 Oct. 1982, now abandoned, which in turn was a continuation-in-part of patent application U.S. Ser. No. 71,648 filed 4 Sep. 1979, now abandoned.

BACKGROUND OF THE INVENTION

The in vitro cultivation of hepatitis A virus (HAV) eluded all attempts for several decades. The modern era of advances in understanding HAV, which led eventually to in vitro cultivation of the virus, was initiated by the successful transmission of HAV to marmosets [Deinhardt et al., J. Exp. Med. 125, 673 (1967), Mascoli et al Proc. Soc. Exp. Biol. Med. 142, 276 (1973) and Provost et al., Proc. Soc. Exp. Biol. Med. 142, 1257, (1973)], by the characterization of HAV from marmoset serum and liver [Provost et al., Proc. Soc. Exp. Biol. Med. 148, 532 (1975)], and by the detection of HAV in the stools of infected humans by immune electron microscopy (IEM), [Feinstone et al., Science 182, 1026 (1973)].

Progress in cultivating and characterizing the CR 326 strain of HAV in marmosets led to its definition as a picornavirus [Provost et al., Proc. Soc. Exp. Biol. Med. 148, 532 (1975)], to the development of serologic assays for HAV antigert and antibody [Provost et al., Proc. Soc. Exp. Biol. Med. 148, 962 (1975) and Miller et al., Proc. Soc. Exp. Biol. Med. 149, 254 (1975), and to the development of potent preparations of HAV from infected liver of marmosets [Provost al., Proc. Soc. Exp. Biol. Med. 148, 532 (1975), and Provost et al., Proc. Soc. Exp. Biol. Med. 155, 283 (1977)]. Such preparations contained about $10^9$ fifty percent marmoset infectious doses per gram of liver tissue. These findings provided the background for the successful propagation of HAV in cell culture first reported by Provost et al., Proc. Soc. Exp. Biol. Med. 160, 213 (1979).

A disadvantage of the foregoing methods is that they require the use of primates that are not only expensive but in short supply and difficult to obtain. An in vitro cell culture system which did not require virus passage in vivo in a subhuman primate would be a significant advance in this art.

OBJECTS OF THE INVENTION

It is an object of the present invention to provide, by in vitro cell culture of hepatitis A virus, an attenuated hepatitis A virus suitable for use as a vaccine. Another object is to provide a method for propagation of hepatitis A virus which does not require virus passage in vivo in a subhuman primate. A further object is to provide a method for the preparation of hepatitis A antigen for use in vaccines and as a diagnostic antigen. Still another object is to provide an in vitro method for attenuating the virulence of hepatitis A antigen. These and other objects of the present invention will be apparent from the following description.

SUMMARY OF THE INVENTION

Live attenuated HAV modified by passage in susceptible cell cultures, without prior passage in vivo in a subhuman primate, so as to replicate in humans and induce an immune response to protect against typical hepatitis A infection without itself causing any significant symptoms of hepatitis A disease.

DETAILED DESCRIPTION

The present invention relates to the in vitro cell culture propagation of hepatitis A virus and, more particularly, to in vitro cell culture propagation of hepatitis A virus wherein the inoculum is a human clinical specimen containing the virus.

The present invention provides a method for propagating hepatitis A virus wherein passage of the virus in a susceptible non-human primate prior to in vitro cell culture is not required.

According to the present invention a clinical specimen containing hepatitis A virus, e.g. stool extract, saliva, urine, or blood, is used as inoculum to infect a susceptible in vitro cell culture. The cell culture may be formed of primary, or low passage, or continuously cultivated, or transformed cells derived from kidney or liver of human or non-human primate origin or diploid fibroblast cells derived from human or non-human primate lung tissue. Specific examples of suitable cell cultures are low passage cell cultures derived from fetal (FRhK6) or newborn kidney cells from rhesus monkey, cynomolgus monkey, or cercopithecus monkey.

The inoculated cell culture is incubated at a temperature in the range of from about 28° to about 39° C., preferably at from about 32° to about 35° C. for a period of time until positive results are obtained for the presence of hepatitis A antigen; time required may vary from 3–200 days, generally from about 25 to about 100 days. The incubation is carried out in the presence of a nutrient medium which maintains viability of the cells at temperatures permitting propagation of the virus in the cell culture. The nutrient medium may be, for example, Eagle's Minimum Essential Medium (EMEM), Williams Medium E, Medium 199, Dulbecco's Modified Eagle's Medium, RPMI Media or Basal Medium Eagle with from about 0.5 to about 10% fetal calf serum. The cultures are subsequently harvested and serial passages of the vital agent are carried out.

The virus may be additionally propagated by serial passages in diploid fibroblast cells derived from human or non-human primate lung tissue. Propagation is effected through at least about 2 serial passages in the diploid fibroblast cells such as, for example, WI-38 or MRC5 cell lines. Preferably propagation is effected through from about 5 to about 100 passages, and most preferably from about 5 to about 40 passages, in the diploid fibroblast cells. Most preferably, prior to passage in the diploid fibroblast cells the virus is propagated in a cell-culture derived from primary or low passage, continuously cultivated or transformed cells derived from kidney or liver of human or non-human primates. Propagation is effected through from about 2 to about 50 passages in the kidney or liver of human or non-human primates.

This invention allows disease diagnosis by direct virus isolation. Further, it allows the in vitro cultivation of the virus in adequate quantity and with appropriate properties for the preparation of live, attenuated or killed, inactivated human vaccines or for use as a diagnostic antigen. A live, attenuated vaccine virus is a virus that is able to replicate in a host animal or a human being without producing disease symptoms while maintaining the capacity to induce an immune response and thus to provide protection against hepatitis A disease. A killed, inactivated vaccine virus is a virus that is unable to replicate in cell culture, a host animal or a human being but which, upon injection in sufficient mass, is capable of inducing an immune response and thus protecting against hepatitis A disease.

The following examples illustrate the present invention without, however, limiting the same thereto.

EXAMPLE 1

A. A 20 percent extract of human stool in PBS was prepared from acutely ill human hepatitis A patients and clarified by centrifugation. It gave an immune adherence hemagglutination titer of 1:16 for hepatitis A antigen. It was further diluted 1:5 in cell culture medium containing 0.5% fetal calf serum and filtered through a 0.45 µ Millipore filter. One ml of this material was inoculated per 25 cm$^2$ flask of fetal rhesus kidney (FRhK6) cells. The inoculum was left in place for 4 hours and then removed. Five ml of EMEM containing 0.5% fetal calf serum plus neomycin and glutamine were added per flask and the medium removed and renewed at 5–7 day intervals with incubation at 32°–35° C. Coverslips were removed periodically and examined by the direct immunofluorescence technique (Provost et al., P.S.E.B.M., 160, 213–221, 1979) for HAV. Such examination was essentially negative until day 33 post inoculation, when the first clear positive results were obtained. The cultures were subsequently harvested at day 37 and the cells disrupted by freeze-thawing and sonication. Cellular debris was removed by low speed centrifugation. The supernatant product gave a positive result for HAV by radioimmunoassay.

B. A successful hepatitis A virus isolation was also accomplished with a second human stool sample which was the origin of strain CR326F. This stool gave a positive result for hepatitis A antigen by radioimmunoassay. The stool sample was diluted and inoculated into cell culture in the same manner as described above. Immunofluorescence revealed the first positive results at day 53 post inoculation. The cultures were harvested at day 53 post inoculation and also gave a successful result for HAV antigen by radioimmunoassay.

EXAMPLE 2

A second passage of the virus from part A of Example 1 was achieved by inoculating 0.5 ml of the supernatant product from Example 1 into fresh FRhK6 cell cultures that were handled comparably to those above. Fluorescence antibody examination revealed the first clear evidence of virus presence at day 15 post-inoculation. The cultures were harvested at day 19 post-inoculation and the product gave a positive result for HAV by radioimmunoassay. Additional serial passage of the virus was carried out in cell culture, i.e., passages 3, 4 and 5. By passage 5, heavy virus growth occured as early as 7–14 days and the virus harvest at day 13 gave strong positive immune adherence (IA) and radioimmune assay (RIA) hepatitis A antigen results.

In similar manner a total of 15 serial passages of strain CR326F HAV (Ex. 1, Part B) were also accomplished. Throughout the course of passaging vital growth became more rapid and productive. At passage 15 virus was harvested at day 8 and HAV vital antigen was detected by immune adherence hemagglutination and radioimmunoassays.

EXAMPLE 3

Antigen, 0.05 ml, obtained as described in Example 2, was incubated with human convalescent hepatitis A sera, 0.02 ml of a 1:20 dilution. The mixture was incubated at 37° C. for 1 hour and then held at 4° C. for a period of three hours. A drop of the material was placed onto a carbon-coated, 300-mesh copper grid, and allowed to adsorb for 30 seconds. The grid was then stained for 2 minutes with 2% aqueous phosphotungstic acid, pH 6.0 (adjusted with 1N KOH) and examined in a Philips 300 electron microscope at 80 KV. After reaction with hepatitis A antibody, characteristics halos of antibody molecules were seen to surround the numerous 27 mµ HAV particles and to bind them into an immune complex.

EXAMPLE 4

The final infected cell culture harvests obtained from Example 2, prepared under aseptic conditions, were treated with 1:4000 formalin at 37° C. for 72 hours. Excess residual formalin was neutralized with sodium bisulfite. All treatments were performed under aseptic conditions. The product was stored at 4° C. Subcutaneous or intramuscular injection of 4 doses of 1 ml given at 2 week intervals into *S. mystax* marmosets and guinea pigs induced circulating hepatitis A antibody in these animals. Further, the marmosets were rendered resistant to challenge with virulent doses of hepatitis A virus. Thus, the ability to make an inactivated hepatitis A vaccine from HAV grown in cell culture as in Examples 1 and 2 was demonstrated.

EXAMPLE 5

HAV derived as in Example 1 was serially passaged a total of 15 times in FRhK6 cell cultures at 35° C. as described in the second paragraph of example 2. The virus harvest from passage 15 was then successfully propagated in fetal human diploid lung fibroblast cell cultures (MRC5) at 35° C. A total of 8 serial in vitro passages of the virus in MRC5 including 3 limit dilution passages were carried out. This yielded HAV variant F. Variant F was found to be attenuated in virulence for both marmosets (*S. labiatus*) and chimpanzees in that intzavenous inoculation of 1 ml of 1:10 dilution and 1 ml of undiluted virus, respectively, into these animals produced serum enzyme elevations in only 1 of 6 marmosets and none of 2 chimpanzees and only minor changes in liver histopathology, while at the same time eliciting a hepatitis A antibody response in all animals. All animals inoculated with the attenuated virus resisted challenges with 1000 50% infectious doses of virulent hepatitis A virus injected intravenously. Thus the cell culture-passaged HAV variant F constitutes a live, attenuated hepatitis A vaccine.

EXAMPLE 6

Hepatitis A virus derived as described in Example 1 and the second paragraph of Example 2 and in Example 5 was serially passed 15 times in FRhK6 cell plus 16 times in MRC5 cell cultures at 35° C. to yield Variant F'. Variant F' was purified by 6 limit dilution passages. Variant F' was diluted 1:10 in phosphate-buffered saline (PBS) and inoculated intravenously into 6 young adult Saguinus labiatus marmosets. The animals were bled weekly for 12 weeks and again at 18 weeks. None of the 6 animals that received variant F' showed elevated serum isocitric dehydrogenase levels and 4 of these 6 animals developed antibody to hepatitis A. All animals that seroconverted were immune to infection when challenged intravenously with virulent EAV. Two chimpanzees were inoculated with undiluted variant F'. Neither showed evidence of hepatitis but both developed antibody to hepatitis A. Thus, this cell culture-passaged HAV Variant F' also constitutes a live attenuated hepatitis A vaccine.

EXAMPLE 7

A lot of live attenuated hepatitis A vaccine was made from Variant F at virus passage level 10 in MRC5 cells. A lot of live attenuated vaccine was made from variant F' at virus passage level 18 in MRC5 cells. Both vaccines behaved in marmosets and chimpanzees in manner comparable to those described in examples 5 and 6. Further, both vaccines were clinically evaluated by parenteral administration in human volunteers without inducing disease. Both vaccines gave a high rate of antibody induction but vaccine F produced possible minor transient serum enzyme elevations in a small portion of recipients. No evidence of serum enzyme elevations was seen in recipients of vaccine F'. Thus both variants F and F' are live attenuated hepatitis A viral vaccines for human beings as well as for *S. labiatus* marmosets and chimpanzees.

What is claimed is:

1. A process for making a hepatitis A vaccine which comprises culturing an inoculum of HAV which has not been passaged through a non-human primate, wherein the culturing occurs in (i) primary, continuously cultivated, or transformed cells derived from kidney or liver tissue of non-human primate origin; and (ii) diploid lung fibroblast cells derived from human lung tissue.

2. A process for making a hepatitis A vaccine comprising:
   a) culturing hepatitis A virus which has not been passaged through a non-human primate and which has been passaged in primary or continuously cultivated or transformed cells derived from kidney or liver tissue of non-human primate origin, or diploid fibroblast cells derived from human or non-human primate lung tissue;
   b) harvesting the cultured HAV; and
   c) inactivating the harvested HAV to make a vaccine.

* * * * *